United States Patent
Bray et al.

(10) Patent No.: US 6,674,292 B2
(45) Date of Patent: Jan. 6, 2004

(54) MICROWAVE CORROSION DETECTION SYSTEMS AND METHODS

(76) Inventors: Alan V. Bray, 19300 Crosswind Cir., Spicewood, TX (US) 78669; Gary R. Schmidt, 6105 Shadow Mountain Dr., Austin, TX (US) 78731; Alfonso Cuevas, 3804 Tamarack Trail, Austin, TX (US) 78727; Victor Dube, 1550 US 290 E., McDade, TX (US) 78650

( * ) Notice: Subject to any disclaimer, the term of this patent is extended or adjusted under 35 U.S.C. 154(b) by 11 days.

(21) Appl. No.: 10/047,672

(22) Filed: Jan. 14, 2002

(65) Prior Publication Data

US 2003/0132760 A1 Jul. 17, 2003

(51) Int. Cl.$^7$ ............................................... G01R 27/00
(52) U.S. Cl. ....................................... 324/637; 324/643
(58) Field of Search ............... 73/24.04, 73; 250/341.1, 250/341.8; 324/637, 640, 642, 643, 700

(56) References Cited

U.S. PATENT DOCUMENTS

| | | | |
|---|---|---|---|
| 5,508,203 A | * | 4/1996 | Fuller et al. ............... 436/149 |
| 5,514,970 A | * | 5/1996 | Marshall .................... 324/632 |
| 6,198,293 B1 | * | 3/2001 | Woskov et al. ............. 324/637 |
| 6,411,105 B1 | * | 6/2002 | Liu ............................ 324/639 |

* cited by examiner

Primary Examiner—N. Le
Assistant Examiner—Vincent Q. Nguyen
(74) Attorney, Agent, or Firm—Luis M. Ortiz; Kermit D. Lopez

(57) ABSTRACT

Corrosion, mold and moisture can be detected under outer layer of structures, such as surfaces associated with vessels and/or buildings, using nondestructive evaluation (NDE). Characterizing the dielectric properties of materials associated with a target can be executed by directing primary microwave energy from a source towards a target, receiving secondary microwave energy signals returned from the target, analyzing the secondary microwave energy signals, and characterizing dielectric properties of materials associated with the target based on analysis of the secondary signals. A system for non-destructively characterizing a target material's dielectric properties can includes a microwave energy source, a waveguide for directing microwave energy towards a target, a receiver for receiving microwave signals reflected off targets, an analyzer for assessing the difference between incident and reflected microwave signals to determine the presence of corrosion within a target or a targeted area, and an indicator for providing results of analysis.

39 Claims, 10 Drawing Sheets

MICROWAVE CORROSION DETECTION SYSTEMS AND METHODS

TECHNICAL FIELD OF THE INVENTION

The present invention is generally directed to corrosion, mold and/or moisture detection and, more particularly, the present invention is related to systems and methods for carrying out corrosion, mold and/or moisture detection utilizing microwave energy. The present invention employs microwave energy to non-destructively characterizes the dielectric properties of materials so as to be able make a determination of any presence or absence of byproducts of corrosion, mold and/or moisture, and can also enable assessment as to the bonding quality of paint onto metallic surfaces.

BACKGROUND

Corrosion of aluminum and steel is a complex situation when considering its effect and impact on military, commercial and industrial vessels and equipment. The U.S. Navy, for example, operates its aviation assets in extreme environments, which can result in staggering annual costs associated with corrosion remediation and repair. Like the federal aircraft fleet, the commercial aircraft numbers are staggering when viewed as a single market. Both military and commercial aviation operators are currently testing vinyl appliqué as an alternative to paint. One of the criticisms of appliqué in corrosive environments is the relative difficulty of inspecting for corrosion through the film-like material.

There is no known nondestructive evaluation (NDE) tool currently available that can detect corrosion under paints and appliqués. What is currently needed are corrosion detection systems and methods that do not require some removal of the paint or appliqué system in order to effectively and accurate accomplish detection of corrosion, especially with complex, high-demand systems such as military aircraft.

The present inventors herein disclose microwave-based corrosion detection systems and methods useful for nondestructive evaluation of targets. The present technology can consider the interaction between incident microwave radiation and the dielectric materials on the surface of the inspected item, including corrosion products, paints, and appliques, to detect the presence of corrosion. The ability of any corrosion detection system to sense corrosion in its earliest stages in aircraft applications, for example, is an important benefit of an NDE system. The savings available by using a condition-based maintenance approach to coating maintenance, for example, is potentially large.

BRIEF SUMMARY OF THE INVENTION

In accordance with the present Nondestructive evaluation (NDE) systems and methods, corrosion, mold and/or moisture can be detected under outlayers of structures, such as surfaces associated with vehicles or buildings. For example, moisture and/or corrosion under paint and appliques found on military and commercial aircraft can be detected using the microwave energy as described herein. Furthermore, moisture, mold and/or corrosion can be found within sublayers, underlayers and/or covered areas associated with materials, walls, ceilings, floors and/or any other structures known in the building construction industry, using microwave energy as disclosed herein. For purposes of the following disclosure, "corrosion" can be interpreted to include mold and moisture and other foreign matter not intended to be associated with a given target. Corrosion can also include improperly applied or defective materials (e.g., poorly-bonded paint-to-target surface). This condition would ultimately lead to increased susceptibility to moisture ingress and corrosion if undetected and/or repaired. Furthermore, for purposes of the following disclosure, the term "target" can be interpreted to refer surfaces, materials, and/or systems of vessels (e.g., boats, airplanes, land-based vehicles) and buildings.

In accordance with one aspect of the present invention, microwave corrosion detector (MCD) technology enables NDE/assessment through the interaction of microwaves and dielectrics such as paints, appliqués, sublayers and corrosion associated with evaluated targets. The present invention assesses the difference between incident and reflected (backscattered) microwave signals against a target to determine the presence of, or damages caused by, corrosion within a target or a targeted area associated with a target. It should be appreciated that word "corrosion" as referred to throughout the disclosure is intended to mean both corrosion and induced by corrosion.

In accordance with another aspect of the present invention, a method for non-destructively characterizing the dielectric properties of materials associated with a target is provided. The method can direct primary microwave energy from a microwave source towards a target; receive secondary microwave energy signals (backscatter) returned from the target; analyze secondary microwave energy signals; and characterize dielectric properties of materials associated with said target based on the analysis of the secondary microwave signals.

In accordance with another aspect of the present invention, a system for non-destructively characterizing the dielectric properties of materials associated with a target is provided. The system can include a microwave energy source, means for directing primary microwave energy towards a target, a receiver for receiving and measuring secondary microwave energy, a microprocessor programmed for analyzing the secondary microwave energy, and means for providing results of microprocessor analysis.

In accordance with another aspect of the present invention, a portable, hand-held system is provided for carrying out MCD inspections. The system can easily detect corrosion for maintenance or monitoring purposes.

In accordance with another aspect of the present invention, a system can non-destructively characterize the dielectric properties of materials so as to be able to determine presence or absence of byproducts of corrosion, as well as the quality of bonding of paint to metallic surfaces.

In accordance with another aspect of the present invention, a system can detect corrosion under painted aircraft surfaces without the need to strip the paint.

In accordance with another aspect of the present invention, a system can detect corrosion under painted surfaces such as petrochemical storage tanks without the need to strip the paint.

In accordance with another aspect of the present invention, a system can detect corrosion under aircraft surfaces covered with vinyl films and appliqués without the need to remove the films or appliqués (e.g., NDE).

In accordance with another aspect of the present invention, a system can detect corrosion around fastener heads on aircraft surfaces without the need to remove paint or appliqué films that would otherwise obscure the corroded areas from visual or optical inspection.

In accordance with another aspect of the present invention, an evaluator can discriminate between paint that has properly bonded to metallic surfaces and that which has not.

In accordance with another aspect of the present invention, a system can detect the presence of moisture in composite aircraft structures such as fuel tanks, radomes and control surfaces.

In accordance with another aspect of the present invention, a system can non-destructively detect the presence of moisture in building materials such as wood and gypsum wallboard.

DETAILED DESCRIPTION OF PREFERRED EMBODIMENTS

Figure 1:
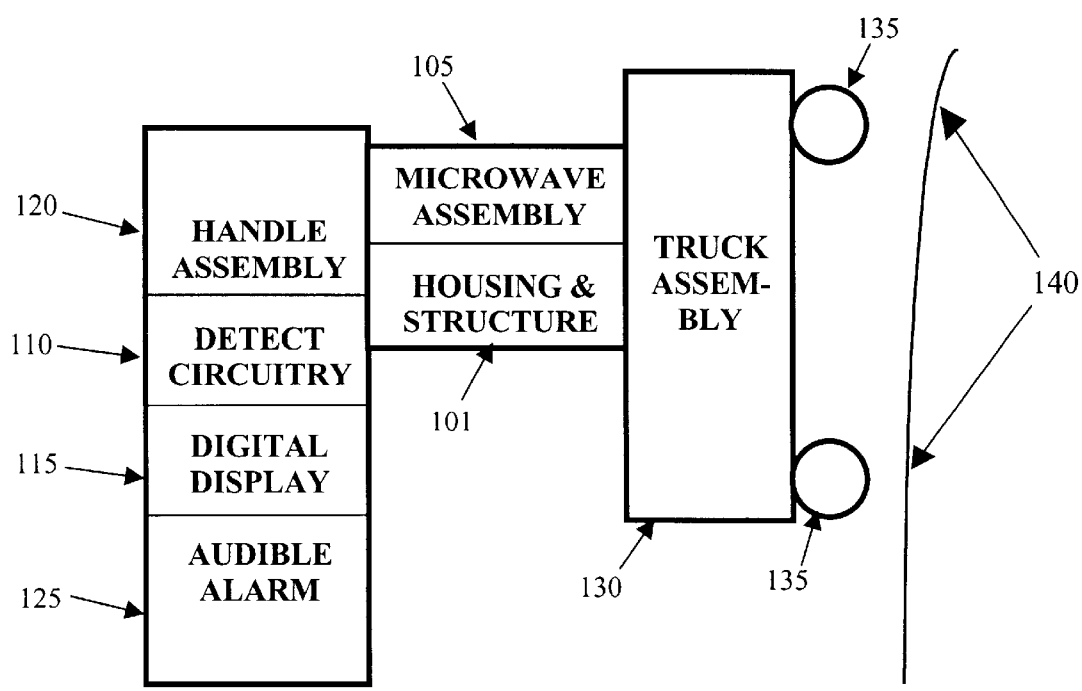
FIG. 1 illustrates a block diagram of components that can be associated with an MCD inspection tool in accordance with teachings of the present invention.

A nondestructive evaluation (NDE) tool that detects corrosion under paint and appliques in military and commercial aircraft is herein disclosed. Generally referred to herein as Microwave Corrosion Detector (MCD) technology, methods and system of the present invention utilize the interaction of microwaves and dielectrics associated with paints, appliques, corrosion, moisture and mold in carrying out target analysis. An MCD tool can use the difference between incident and reflected microwave signals to determine the presence corrosion on or about a target. For purposes of the present detailed description of the invention, "corrosion" should be interpreted to include mold, moisture and other foreign matter not intended to be associated with a given target. Corrosion can also include improperly applied or defective materials (e.g., poorly-bonded paint-to-target surface). Improperly applied or defective materials can ultimately lead, for example, to increased susceptibility to moisture ingress and corrosion if undetected and/or repaired. "Target" as referred to herein can be interpreted to include vessels, (e.g., boats, airplanes, land vehicles), buildings, structures and other man-made objects or materials. It is a desired aspect of the present disclosure to teach the skilled the essential elements of an easy-to-use handheld MCD target inspection tool that can detect corrosion for maintenance or monitoring purposes.

The MCD inspection device can be a hand-held portable device which can detect corrosion under painted and appliqued surfaces associated with a target. The invention can detect, for example, galvanic, exfoliation, and pitting corrosion products. The device can be scanned, for example, over an aircrafts surface while being held by one hand. Audible and/or visual alarms can be used to indicate corrosion is present. For example, a light bar can further be used to indicate the level or intensity of corrosion on a 1–10 scale. It should be appreciated by those skilled in the art that more elaborate information displays and data enabling technology can also be incorporated into the invention to render assessment results without departing from the scope and teaching of the invention. For example a microprocessor and liquid crystal display may enable additional data processing and visual assessment capabilities to a user of the invention; however, additional user interface technology such a microprocessors and screen displays add cost and weight to the overall device. The device can also record results utilizing memory technology (device-based or removable) also well known in the art. A portable, hand held device can be powered, for example, by 5 volt DC power source and can run on batteries or rectified line power. A standard K band transmitter can be considered as a commodity part of the device and is well known for its employment within police radar guns.

Maintenance personnel should be able to use MCD inspection tools to locate and classify corroded areas under coatings, and make condition based maintenance decisions about repainting, maintenance actions, damage monitoring, and, if necessary, disassembly for deep inspection. Simplified training and low cost for MCD inspection tools can enable widespread deployment in the most maintenance centers, which can thus eliminate much uncertainty associated with aircraft corrosion control.

Some of the predominant components of a MCD inspection tool are illustrated in the block diagram of FIG. 1. The microwave assembly 105 can be considered as the guts of the MCD inspection tool 100. The detection circuitry 110 and display(s) 115 can be integrated into a handle 120 integrated with the inspection tool 100. The handle 120 can also house an audible alarm 125. With the illustrated configuration, the microwave assembly 105 can generally be in a bridging structure between an optional truck assembly 130 and the handle assembly 120. This can include a housing 101 to protect and shield the microwave assembly 105 and a structural interface strong enough to be a rigid connection for the entire tool assembly.

A housing 101 for the MCD tool 100 can take many portable forms. Those skilled in the art can appreciate that a MCD tool 100 can be provided in a radar-gun-like structure, radiation monitoring unit configuration, or can also take the form of metal-detector units. The system can also optionally include a truck assembly 130. The truck assembly 130 would provide two major functions: (1) enable easy, well balanced, scanning motion and; (2) keep the waveguide within a given tolerance of the target surface 140 being inspected. Rollers 135 can also be provided with the truck assembly 130 to provide both distance and ease of use in scanning over targets surfaces. Some contours may require changing the truck assembly 130. As an example an inside corner inspection of a target can be accomplished by utilizing a wedge shaped truck assembly 130.

Figure 2:
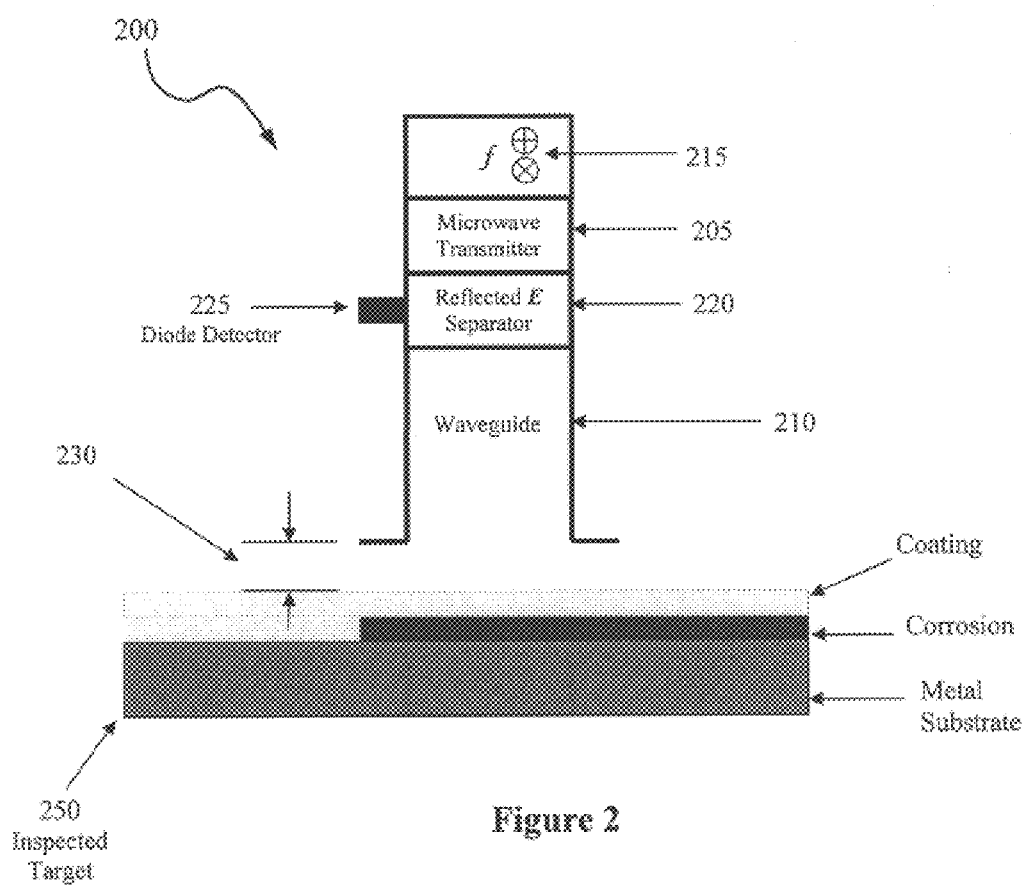
FIG. 2 illustrates a block diagram of a nondestructive evaluation sensor and associated components in accordance with teaching of the present invention.

The basic design of a microwave assembly in an NDE sensor can be relatively simple. FIG. 2 illustrates the basic components of microwave NDE sensor 200. A microwave Transmitter 205 is the source of microwave energy for the device 200 and should generally be matched to a waveguide 210 in frequency. Frequency tuning can be done by adjusting the device's transmitter frequency controls 215, which can be in mechanical and/or electronic form. A reflected energy separator 220 (e.g., Three-Port Circulator) can be used to separate energy reflected from the incident microwave signal. The separator 220 generally does this using a phase comparison techniques because the two signals are phase shifted by reflections. A (Gunn) Diode Detector 225 (diode) can sense radiated microwave energy and convert it to an electrical signal. The waveguide 210, can be constructed or designed as a short (roughly 1–2 inch) section with flanged ends and matchable in size to the transmitter's 205 band. A standoff distancer 230 can maintain the standoff distance from an inspected target 250 and can provide a second tuning degree of freedom for the device 200. As discussed above, standoff distance can be maintained by using a scanning truck assembly (FIG. 1, element 130).

The frequency band, K band or 24 GHz in the aircraft MCD tool case, generally determines the circulator, the detection diode, and the waveguide sizes. These components are generally known as commodity items in microwave catalogs. As a result they are not cost drivers in the design, and good quality (defined by the ability to separate and detect, and tool reliability) devices can be obtained for reasonable cost. A microwave transmitter, however, can be an expensive component. In an NDE device that can be deployed in a portable configuration, it is preferred that the transmitter be battery powered and relatively small. Transmitters can range from full frequency adjustable devices that must be driven by expensive microwave synthesizing equipment, to department store door opener sensors. Door openers, unfortunately, have largely been replaced by infrared sensing devices and are no longer available. The transmitter used in police radar guns is a K band version device and should be available on the market for many years to come.

An issue in the microwave assembly can be found with the associated circuitry. For example, some RF interfaces can get into the signal at the output of the diode. Such a problem can be eliminated by placing blocking capacitors at the circulator output. Frequency tuning for the device can be provided by electrical or manual timing. Furthermore, standoff distance is an open-minded waveguide is essentially a tuning parameter, and the output of the device varies as standoff is charge.

A series of experiments were conducted by the present inventors to determine the optimal standoff distance for maximizing reflected signal amplitude. Tests involved fabricating wooden spacers from 2 to 20 mm in thickness and testing the invention at each distance. A 7-mm standoff produced the highest signal to noise ratio and was then used throughout the project. The standoff optimization was repeated after frequency tuning voltage was added, but the value for maximizing signal to noise remained at 7 mm. Once optimal standoff distance is determined, it may be preferred that the standoff distance is maintained by a scanning truck. The scanning truck can provide for distal adjustments mechanically using means known in the art. For example, standoff distance can be accomplished by using small wheels 135 in a truck assembly 130 as shown in FIG. 1 that adjustably suspend the device roughly 7 mm above the inspected target. Since high probability corrosion areas are often in corners or joints, it may also be necessary to provide a trolley so that alternate truck shapes can be adapted to the tool for use in diverse areas.

Both tuning and power voltage can be obtained from the same power source. This can be carried out using a relatively simple voltage splitting circuit that can yield 14.1 and 5-volt signals from a battery or AC rectifier of approximately 24 volts. Tuning can also be fixed during manufacturing and during factory acceptance testing (FAT).

A visual and/or audible alarm/detection circuit (not shown, but generally known in the art) can be designed and built to interpret the output of, for example, the Gunn diode, and would be useful for corrosion intensity or level evaluation. The output of the Gunn diode in a pre-prototype test carried out by the present inventors was approximately 35 mV for a heavily corroded area, and 45 mV for an uncorroded area. Through filtering, automatic gain control (AGC), and classic signal processing/display circuitry the minimization of false positives and the accuracy of a corrosion present notification can be greatly enhanced. Generally the signal to noise ratio associated with corrosion detection is directly proportional to the difference between the uncorroded background and the signal from the corroded substrate.

The threshold circuitry useful in the present invention is fairly common in other sensing devices such as a stud finder. The cost of the threshold circuitry shouldn't be a driving factor in unit cost because the only detection metric in an MCD is voltage amplitude and trend. The trend issue comes from the fact that corrosion is always sensed as a decrease in signal strength. It is this property that makes the use of an AGC circuit appropriate.

Figure 3:
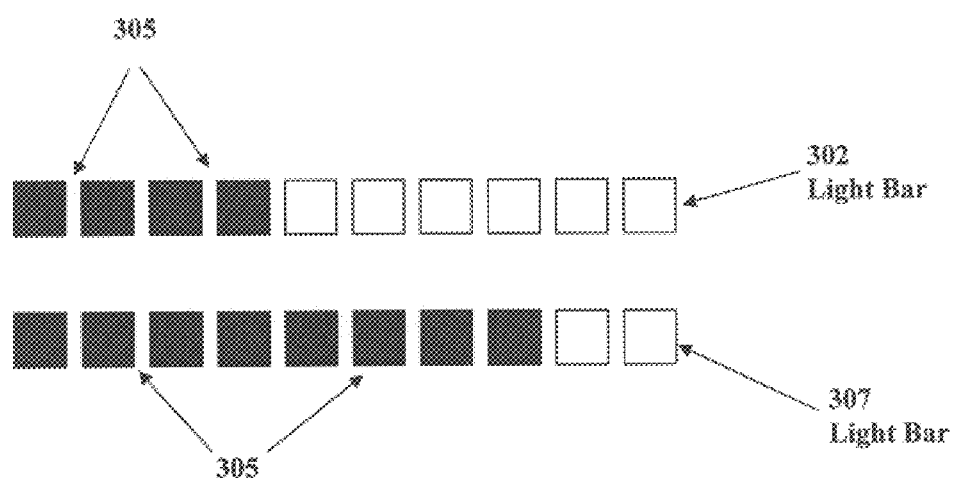
FIG. 3 illustrates corrosion indicators that can be utilized in accordance with the teaching of the present invention.

The display circuitry is envisioned as a light bar indicating corrosion intensity. A light bar series might look something like that illustrated in FIG. 3. The number of lights turned on can be based on the threshold circuit output that in turn begins at the output of the Gunn diode. For example, if lights 305 are lit along the light bar 302, then less corrosion is indicated. But if more lights 310 are lit along the light bar 307, then more corrosion may be indicated. The display size and power requirements can be determined based on variable housing designs. The length of a light bar like that shown above can be on the order of 1.5–2.5 inches, and can sit atop and be integrated with a handle of MCD inspection tool. It may be worthwhile to include an output port for recording the data as it's collected.

Power requirements can be expected to be on the order of 24 V and under 0.5 watts, and could be simple batteries that would allow periods of operation to 2–3 hours. This power requirement is well within the range of modern rechargeable tool technology and is a more practical option than batteries for MCD sensor power. A simple 110 V line cord is probably the most reliable, lowest cost option, and avoids recharge down times, but limits mobility. If the operational environment is suited to a 110 V line its advantages in reliability and cost make this an attractive option.

Figure 4:
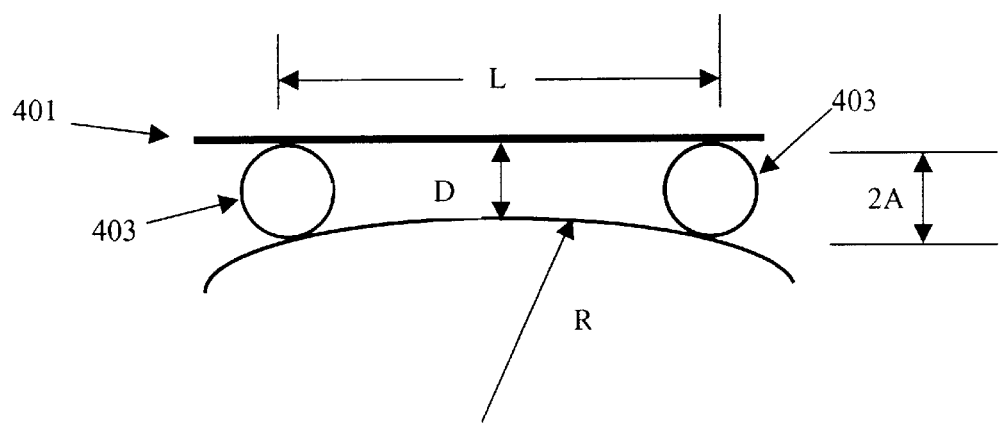
FIG. 4 illustrates a block diagram of geometric considerations for a truck assembly that can be utilized in carrying out the methods and systems of the present invention.

Dimensional properties that can be considered for a truck, handle and structure design and can be integrated into the MCD inspection tool are depicted in FIG. 4. The truck assembly 401 can include maintaining the waveguide termination suspended above the surface being inspected at a distance of D±1.5-mm. Although the standoff, D, was 7-mm in a pre-prototype device, it should be appreciated that the distance can change as a result of changes in the final optimized microwave assembly. A "logical 0" signal can be provided to the device's readout electronics when the distance to the inspection surface is outside the limits set above, and a "logical 1" otherwise. This condition can necessitate the use of a proximity sensor installed in the truck to measure the distance from the sensor to the inspection surface (D in the example below). The truck can be constructed such that the suspension height variance of 1.5 mm is rarely violated when all wheels 403 are in contact with the target 410. The radius of curvature of the surface inspected—R, the wheelbase—L, wheel radius A, and the suspension distance—D, are shown in the sketch of FIG. 4. As the wheel base (L) increases the suspension height (D) becomes smaller for a fixed curved surface radius (R). This relationship can be mathematically expressed as:

$$D=2A-R+(R^2+L^2/4)^{1/2}$$

Figure 5:
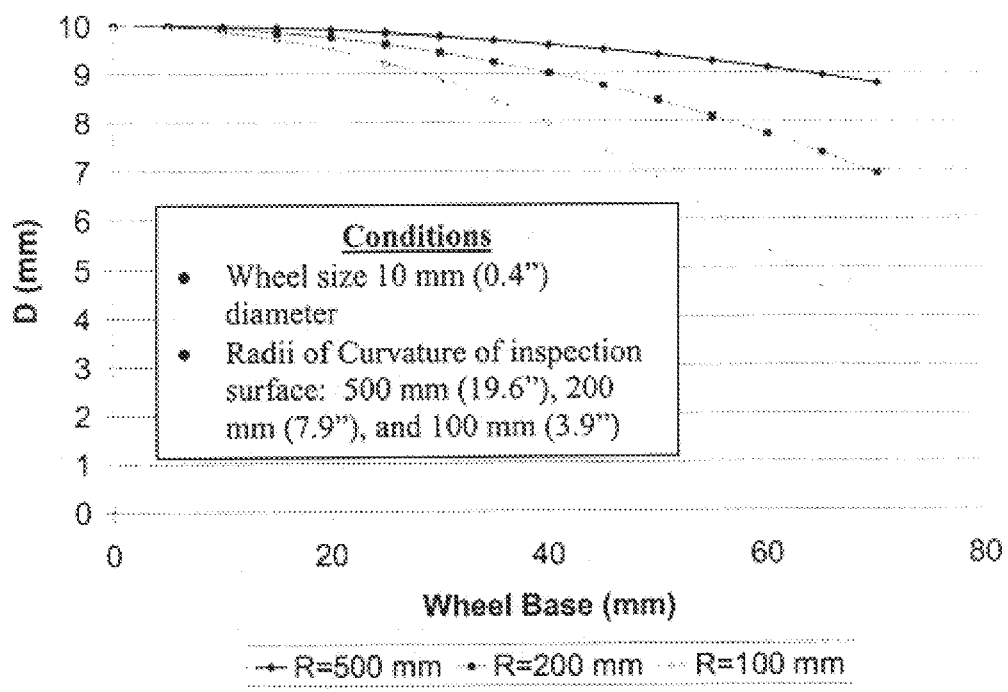
FIG. 5 is a graph illustrating distance measurements to an inspected surface as a function of a truck assembly's wheelbase for a wheel of 10 mm diameters at three curvature levels.

FIG. 5 shows D as a function of the wheelbase length L. The truck wheel size in the example was chosen as a 5-mm radius wheel (10-mm diameter, or 0.4 inches). The error in assuming D is 10 mm (2A) doesn't reach 1.5 mm (D=8.5) until the radius of curvature of the inspection surface is approximately 100 mm (≈4 inches) for a truck wheelbase of 35 mm (about 1.4 inches).

Design relationships such as the one illustrated in the FIG. 5 can be utilized to size the truck. Competing factors such as stability, which call for a large wheelbase, and the potential error in standoff distance D, which call for a small wheelbase, may be traded off in the truck design.

Figure 6:
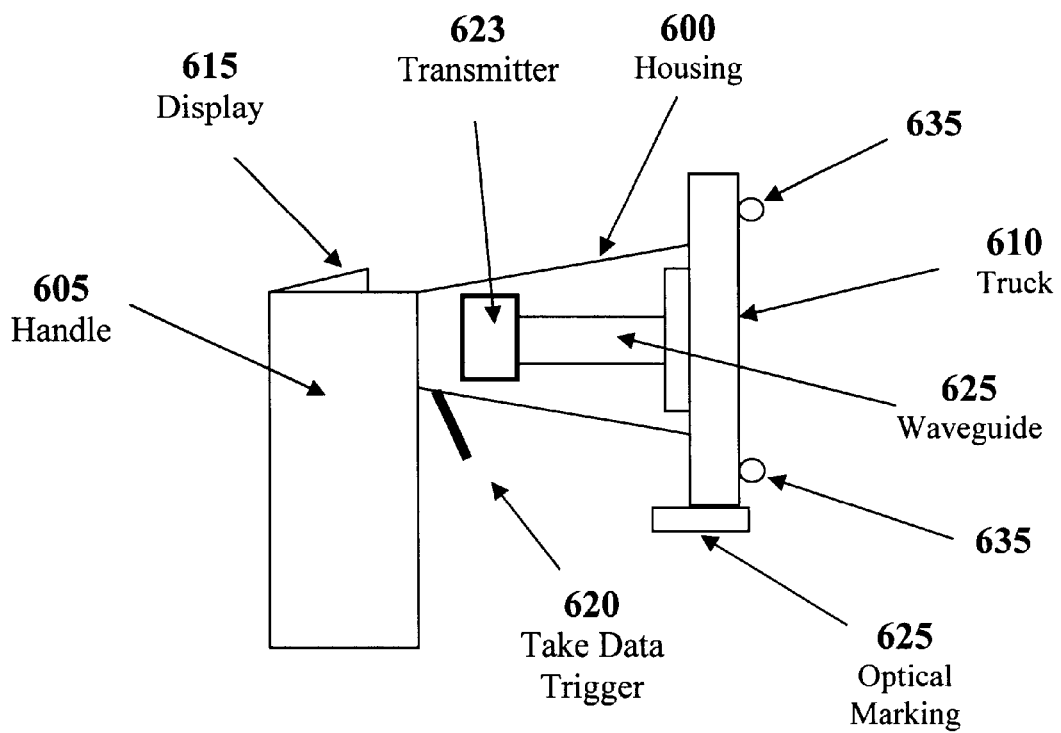
FIG. 6 illustrates a block diagram of a system including a truck assembly, handle, housing and sensor components in accordance with a preferred embodiment of the present invention.

The truck should be easy to move in a scanning motion. A handle 605 can be integrated into the truck in manner somewhat like that shown in FIG. 6. A handle 605 allows an operator to easily guide the truck 610 along the surface of a target. Detection electronics and associated display/alarms can be built into handle 605, with a display 615 preferably sitting in an area above the handle's 605 handgrip area. Audible alarms (not shown) can take two forms—either "corrosion indicated," or "don't take data." The latter would be the case when a trigger 620 is pulled while the truck 610 is not in proper contact with the target/surface being inspected. The correct balance of weight, size, and moment between the handle 605, truck 610, and waveguide systems 625 can impact the ability for a unit to scan quickly and comfortably.

The housing structure 600 between the truck 610 and the handle 605 has a number of functions. It provides the structural support for the entire assembly, smoothly connecting the truck 610 and the handle 605 with a rigid interface. The housing 600 protects the microwave transmitter 623 and can contain the wiring and connection to the handle 605 detection/display circuitry and any power supply associated with the unit. The housing 600 provides a smooth interface with the truck 610 that places the waveguide associated with the transmitter 623 at an optimal orientation with the inspection area and can enable the ability to change struck features when inside corners or other shapes require it. A system can also, for example, resemble a cordless rechargeable drill with a flat head roughly 1–3 inches on a side. Rollers 635 or wheels can be installed on the truck's surface 610 nearest the potential target for enabling proper contact with the target's surface.

An optional marking device 640 can allow the operator to mark areas where corrosion was most intense. Such as device or solution can be integrated into the present invention. Such functionality could be provided using, for example, inking or tagging mechanisms integrated near the assessment area. The option of having the operator carry a magic marker in their other hand is much cheaper and may be a more accurate approach as it utilizes the operator's integrated information to mark the corrosion locations.

The housing 600 can also include shielding of stray microwave radiation. The transmitter 623 should have already passed UL shielding tests in other applications where commodity transmitters are used (e.g., police radar transmitters). Typically they are low power devices, on the order of $1/100$ to $1/1000$ as powerful as a microwave oven. But each new transmitter application generally must be designed to minimize shielding. The housing 600 materials can include integral shielding materials such as a copper weave or similar approach.

NDE methods take advantage of the way in which incident radiation interacts with layered dielectric media. As the dielectric characteristics under the aperture of the wave guide change, the reflected signal changes. On an aircraft the layers of materials over bright aluminum typically include an anti-corrosion coating, a primer and topcoat, or an applique. These dielectric layers affect the transmission characteristics of the microwave signal in a relatively constant fashion on the skin of the aircraft. If a layer of corrosion products begins to develop on the surface of the aluminum, or in the vicinity of a scratch in the anti-corrosion coating, the dielectric characteristic changes. This in turn changes the reflected signal, and has been demonstrated using corroded steel substrates under paint in a shipboard application. The amount of corrosion required to effect this change is of great interest—if microwave NDE is to be useful in aircraft inspection, sensitivity to early corrosion formation must ideally be achieved.

To examine this sensitivity a series of plaques were placed in corrosive environments for varying times of exposure, and sensitivity measurements made as a function of exposure time. Corrosion types included exfoliation specimens prepared to ASTM G34-90, and galvanic specimens that used an aircraft rivet material as a dissimilar metal in a nitric acid electrolyte. The sensitivity to coating type and corrosion level is assessed by initial detectability and the correlation of detection amplitude with exposure time.

The test sensors were rectangular K band waveguides driven by a tunable microwave source. Sensor sensitivity was driven by two primary factors—frequency and standoff distance from the part being inspected. Typical inspection frequencies were on the order of 24 GHz, with standoff distances on the order of 6–8 millimeters. Sensor output during testing was found to correlate well with time of exposure of the plaques after a certain detectability exposure was reached, and this detectability level varied based on corrosion type, coating type, and the presence of anti-corrosion coatings.

Testing of the present invention consisted of static placements of the MCD device over uncorroded then corroded areas covered by paints and appliques. The goal of the testing was to measure the contrast between signals with and without corrosion beneath a coated surface. This was done in a very simple fashion:

1. A device was placed on that part of the specimen with no corrosion under the coating, and a measurement of diode output voltage was made.
2. The device was then moved to the area with corrosion underneath and another voltage measurement was made.
3. This process was repeated a minimum of 6 times on each side of the specimen, alternating from corroded to uncorroded areas. The corrosion sensitivity contrast metric was taken as the average of 6 or more voltage differences of the form:

$\Delta V_i$=Uncorroded Voltage$_i$–Corroded Voltage

A standard deviation was also computed for the $\Delta V$ measurements. Typical $\Delta V$ values for high corrosion contrast were on the order of 6–10 mV, with a standard deviation of 0.6–1.0 mV. Uncorroded voltage ranged from 35 to 50 mV.

Specimens used during testing included:

Saltwater Galvanic Corrosion Samples—these are 7075 T6 aluminum plates sanded to bare metal prior to exposure. A dissimilar metal, in the form of a bolt made from aircraft rivet material, can be utilized to provide galvanic potential. The exposures include soaking in salt water at room temperature. The saltwater solution can be changed approximately daily to improve dissolved oxygen content.

Nitric Acid Electrolyte Corrosion Samples—like the saltwater samples these are 7075 T6 aluminum plaques with a steel bolt as a dissimilar metal. They are soaked in a nitric acid solution to increase galvanic and other corrosion rates. Production time is on the order of 5 days.

Figure 7:
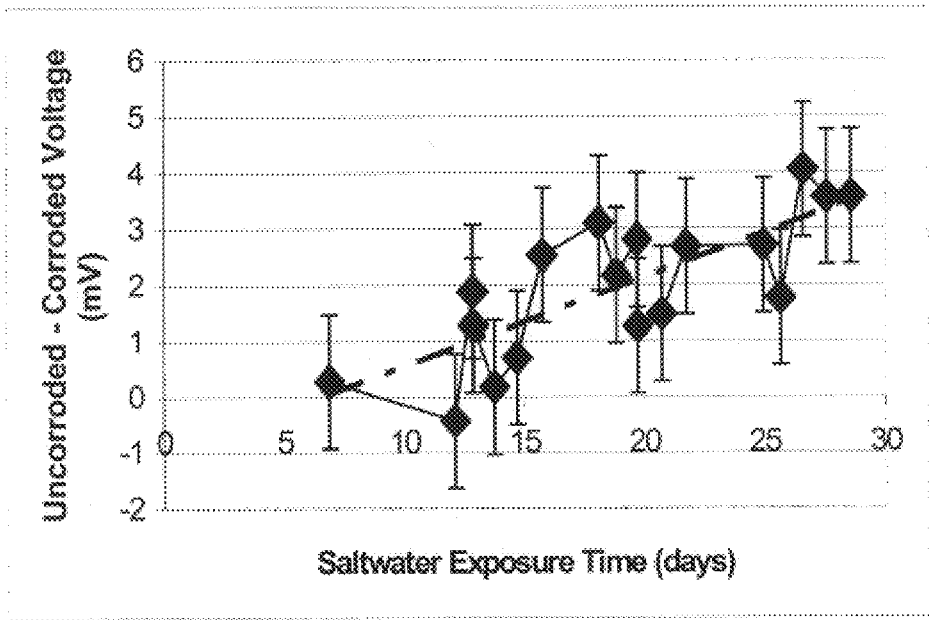
FIG. 7 is a graphical illustration of change in Voltage versus Time of saltwater exposure for scratched 7075-T6 aluminum with an Allodine 1200 coating in accordance with a test procedure carried out utilizing the present invention.

The exposures were performed in a manner that yields samples of varying exposure times. The alpha level prototype measures corrosion presence at a number of exposure times, providing data as a function of corrosion degree. FIG. 7 graphically illustrates the voltage change ($\Delta V$) due to corrosion as a function of time for saltwater specimens. These data were collected on six plaques that were in an out of the baths roughly 5 times each. FIG. 7 includes a best-fit trend line (dotted), which indicates a correlation with exposure time, but the data was also noisy. Despite the noise there was a clear correlation with exposure time, and the detection onset of corrosion for scratched 7075 with an anti-corrosion coating appears to be approximately 17 days.

The origins of the noise in the saltwater data included:

There is a basic random measurement error that over the entire project was approximately 1.0 mV for uncoated specimens, and 0.6 for coated specimens.

The repeated drying, measuring, and inspection of the saltwater specimens may have had some effect on sample corrosion levels. As noted earlier, the repeated inspection of bare metal corroded specimens can wear off corrosion products—a problem that would not occur in the field since the surfaces being inspected are coated.

The saltwater was changed daily except for weekends and a period in the early part of the exposure. This may have led to some sample variation.

The exposure time was limited to 30 days, thus the amount of corrosion was small, and the probe response was limited to around 4 mV. The 60-day exposure planned in Phase II will create a wider range of corrosion degree.

Figure 8:
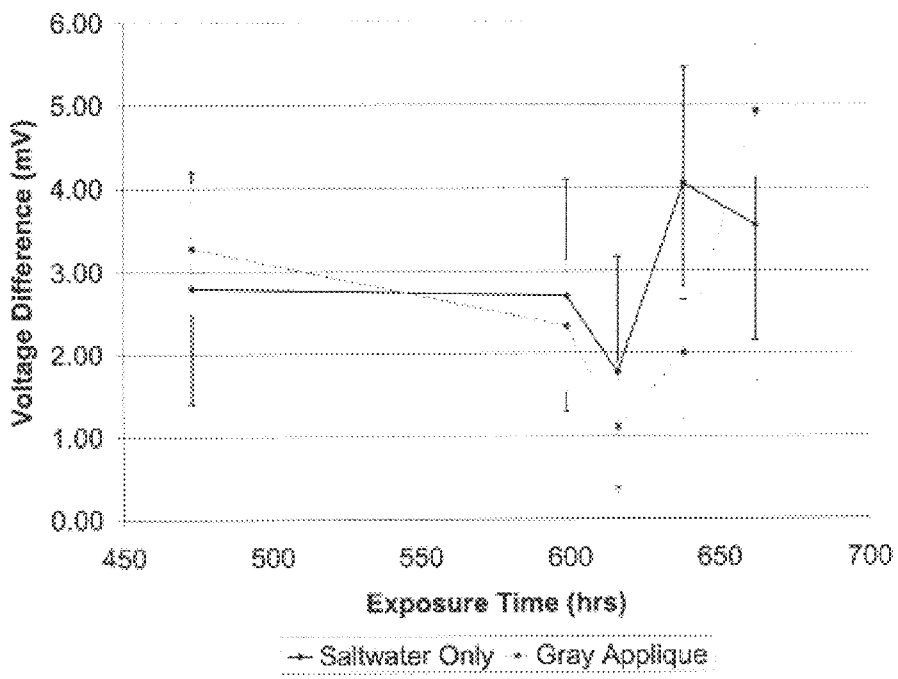
FIG. 8 is a graphical illustration of Bare corroded metal and appliance responses from saltwater specimens in accordance with a test procedure carried out utilizing the present invention.

FIG. 8 graphically illustrates the last data points taken for the saltwater exposed plaques. These plaques were covered with the 3M 1500 Gray Applique and re-measured. Note the correlation of the two curves is very high—low or high corrosion level specimens were still low or high respectively whether coated with the applique or not. This indicates an ability of the MCD technique to penetrate through a coating to discern the degree of corrosion underneath.

The saltwater exposure specimens are the closest example of what might be encountered in a field aircraft inspection. The probe produced an average (the trend line in FIG. 7 signal ($\Delta V$)) of 3.8 mV for bare scratched 7075-T6 specimens with Allodine coating from plaques submerged in saltwater at room temperature for 30 days.

Figure 9:
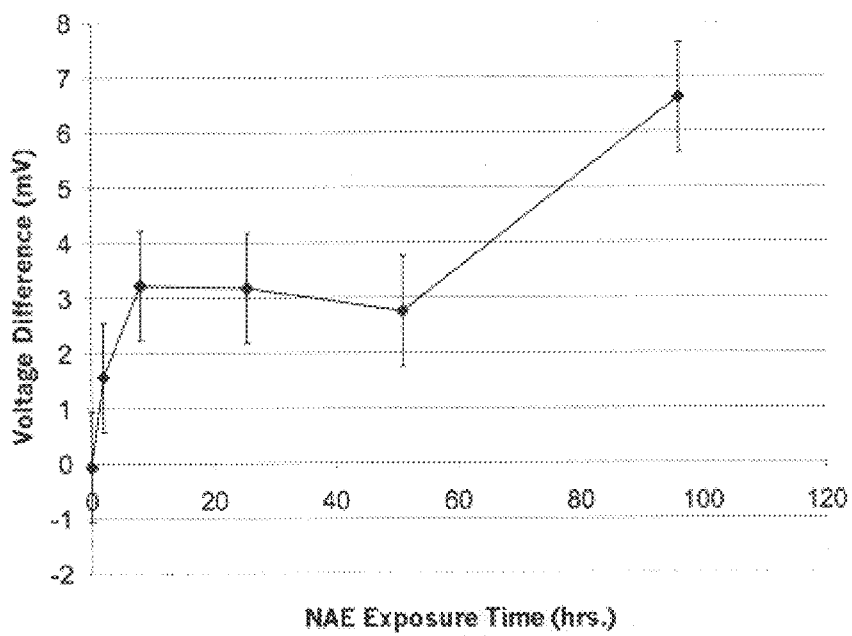
FIG. 9 is a graphical illustration of change in Voltage versus Time of Exposure for Bare Metal nitric acid etched (NAE) samples in accordance with a test procedure out utilizing the present invention.

Nitric acid etched (NAE) exposures were performed using bare metal plaques prior to applying the coating. NAE specimen exposure times ranged from 0 to 96 hours, and can be produced in a repeatable manner. Example $\Delta V$ measurements using the invention are shown in FIG. 9 as a function of exposure time. Although there is some sample induced variation in the data there is still a clear indication that the $\Delta V$ measurements correlated well with exposure time. Standard deviations ranged from 0.5 to 1.0 mV. Detectability was gauged at the point that probe output exceeds 1.5 mV, and this occurred at roughly 8 hours for the NAE bare metal case.

Figure 10:
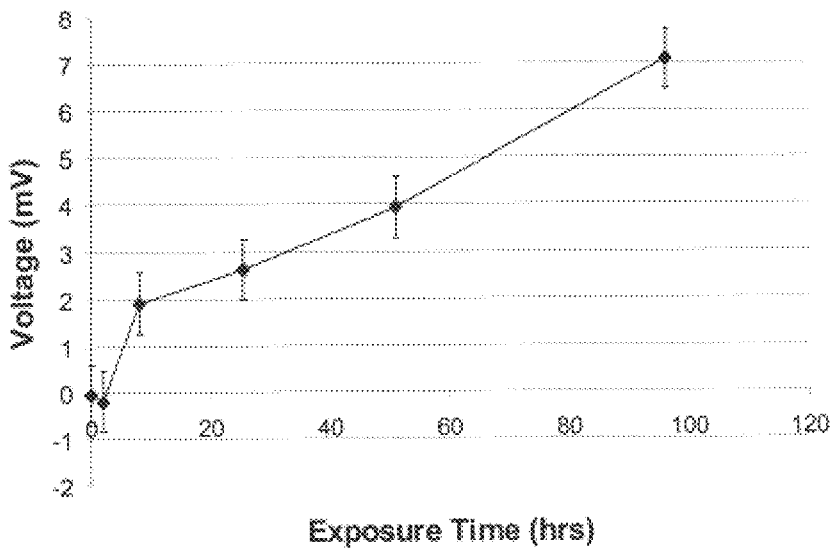
FIG. 10 is a graphical illustration of change in Voltage versus Time of Exposure for NAE samples of described in FIG. 9 and covered with 3M 1500 Flouropolymer Appliques in accordance with a test procedure carried out utilizing the present invention.

FIG. 10 represents a data set collected on the same specimens as those indicated in FIG. 9, but with 3M 1500 flouropolymer appliques applied over the corroded and uncorroded surfaces. Note that the standard deviations are smaller than in FIG. 9. This was always the case—the appliques, and to a lesser extent the paints and primers, had the effect of reducing the standard deviation in the data set. It is assumed that the reason for this is that the coatings reduced the effect of surface roughness and/or altitude on the data. Roughness does contribute to scatter in the data because it changes the distance between the transmitter and the surface, which changes the phase and amplitude of the microwave reflected signal. The dielectric signature of the corrosion is a much larger contributor to the total signal content, but roughness adds scatter and possibly a small amount of systematic error to the $\Delta V$ measurements. An attempt was made to quantify the effect of surface roughness by making multiple measurements on the same corroded surface in a number of locations, and the impact on $\Delta V$ was roughly a 0.2 mV standard deviation. The roughness component seems to go away with a coating and makes the data much more uniform over an inspection surface.

Figure 11:
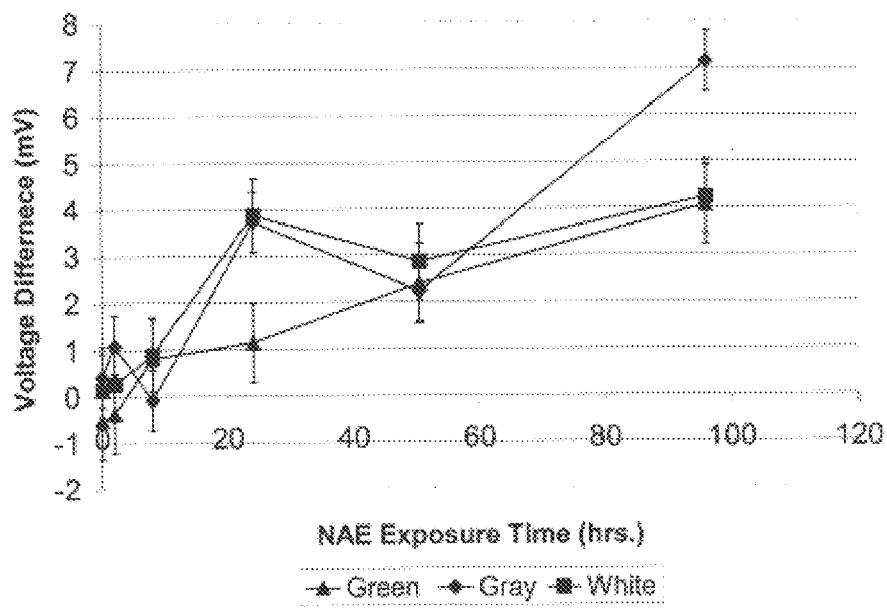
FIG. 11 is a graphical illustration of change in Voltage versus Time of Exposure for NAE samples with two paints and a green primer in accordance with a test procedure carried out utilizing the present invention.

FIG. 11 illustrates the probes response to corrosion under paint. These were single paint layer specimens applied in a spray operation done by Sherwin Williams Inc.—who also provided some of the paints. The green paint comprised a MIL-85582C primer. It had the worst detectability threshold for the NAE specimens at around 48 hours. Gray and white paints allowed detection at roughly 24 hours. White paint was heavily loaded with titanium dioxide ($TiO_2$). Despite this heavy loading it tracked the gray paint until 96 hours, at which point it appeared to have an attenuating effect. Gray paint had the least effect on the data, and the exposure versus time behavior emulated the bare metal condition very closely.

Figure 12:
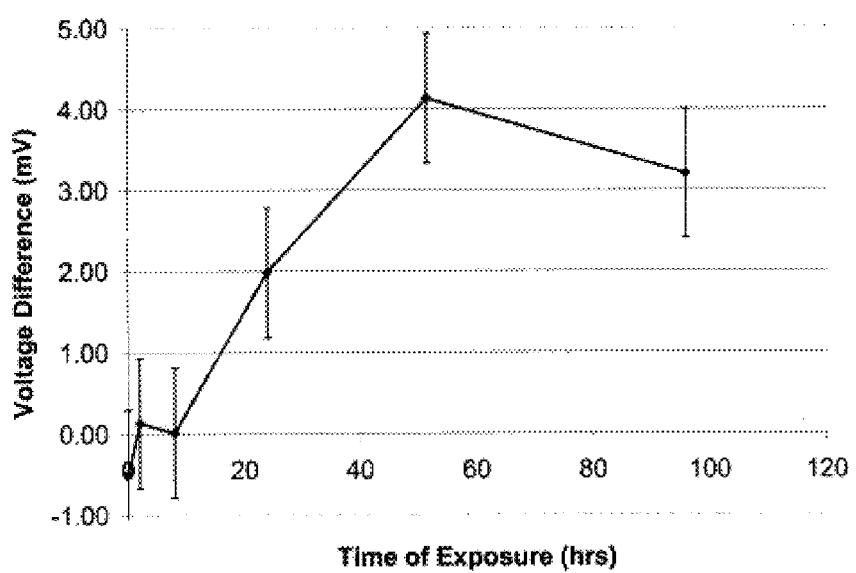
FIG. 12 is a graphical illustration of change in voltage versus Time of Exposure for a combination of primer and gray paint in accordance with a test procedure carried out utilizing the present invention.

It is unclear why the primer (green) had such an attenuating impact on the data. The primer is heavily loaded with chromate, and this is probably the origin of the response difference. Most of the other primer constituents are similar to those in the paints, so the circumstantial evidence points to the chromate content. Despite the somewhat lower response, the probe consistently detected corrosion under the primer, even when another coat of paint was added. FIG. 12 shows the microwave reflected energy when a paint was added atop the (green) primer.

We claim:

1. A method for non-destructively characterizing the dielectric properties of materials associated with a target, comprising the steps of:
    directing primary microwave energy from a microwave source towards a target;
    receiving secondary microwave energy signals returned from said target;
    analyzing said secondary microwave energy signals; and
    characterizing dielectric properties of materials associated with said target based on said analyzing of said secondary microwave signals;
    wherein said steps of analyzing and characterizing are carried out to determine the bonding quality of paint to metallic surfaces associated with said target.

2. The method of claim 1 wherein said steps of analyzing and characterizing are also carried out for detecting the presence or absence of byproducts of corrosion.

3. The method of claim 1 wherein said steps of analyzing and characterizing are also carried out for detecting the presence or absence of byproducts of mold.

4. The method of claim 1 wherein said steps of and characterizing are also carried out for detecting the presence or absence of by products of moisture.

5. The method of claim 1 wherein said steps of and characterizing are also carried out for detecting corrosion and corrosion damage under painted aircraft surfaces without the need to strip paint from said aircraft surface.

6. The method of claim 1 wherein said steps of and characterizing are also carried out for detecting corrosion and corrosion damage under painted surfaces such as petrochemical storage tanks without the need to strip paint from said surface.

7. The method of claim 1 wherein said steps of and characterizing are also carried out for detecting corrosion and corrosion damage under aircraft surfaces covered with vinyl film and appliqués without the need to remove films and/or appliqués from said surface.

8. The method of claim 1 wherein said steps of and characterizing are also carried out for detecting corrosion and corrosion damage around fastener heads on aircraft surfaces without the need to remove said paint and/or appliqué films that would otherwise obscure corroded areas from visual or optical inspection.

9. The method of claim 1 wherein said steps of analyzing and characterizing are also carried out for identifying and discriminating between paint that has properly bonded to metallic surfaces and paint which has not.

10. The method of claim 1 wherein said steps of analyzing and characterizing are also carried out for detecting the presence of moisture in composite aircraft structures including fuel tanks, radomes and surfaces.

11. The method of claim 1 wherein said steps of analyzing and characterizing are also carried out for testing the quality of aircraft coating applied to aircraft surfaces specifically for the purposes of avoiding radar detection.

12. The method of claim 1 wherein said steps of analyzing and characterizing are also carried out for non-destructively detecting the presence of moisture in building materials including wood and gypsum wallboard.

13. A method for non-destructively characterizing the dielectric properties of materials associated with a target, comprising the steps of:
    directing microwave energy from a microwave source towards a target;
    receiving microwave energy signals returned from said target;
    analyzing received microwave energy to determine the difference between incident and reflected microwave signals to determine the presence of corrosion within a target or a targeted area associated with a target; and
    characterizing dielectric properties of materials associated with said target based on said analyzing of said secondary microwave signals.

14. The method of claim 13 wherein said step of analyzing further comprises the step of detecting a presence of absence of by products of corrosion.

15. The method of claim 13 wherein said step of analyzing further comprises the step of detecting the presence or absence of byproducts of mold.

16. The method of claim 13 wherein said step of analyzing further comprises the step of detecting a presence of absence of by products of moisture.

17. The method of claim 13 wherein said step of analyzing further comprises the step of determining bonding quality of paint to metallic surfaces associated with said target.

18. The method of claim 13 wherein said step of analyzing further comprises the step of detecting corrosion and corrosion damage under painted aircraft surfaces without the need to strip paint from said aircraft surface.

19. The method of claim 13 wherein said step of analyzing further comprises the step of detecting corrosion and corrosion damage under painted surfaces including petrochemical storage tanks without the need to strip paint from said surface.

20. The method of claim 13 wherein said step of analyzing further comprises the step of detecting corrosion and corrosion damage under aircraft surfaces covered with vinyl film and appliqués without the need to remove films or appliqués from said aircraft surfaces.

21. The method of claim 13 wherein said step of analyzing further comprises the step of detecting corrosion and corrosion damage around fastener heads on aircraft surfaces without the need to remove said paint and/or said appliqué films that would otherwise obscure corroded areas from visual or optical inspection.

22. The method of claim 13 wherein said step of analyzing further comprises the step of identifying and discriminating between paint that has properly bonded to metallic surfaces and paint which has not.

23. The method of claim 13 wherein said step of analyzing further comprises the step of detecting the presence of moisture in composite aircraft structures including fuel tanks, radomes and surfaces.

24. The method of claim 13 wherein said step of analyzing further includes the step of testing the quality of aircraft coating applied to aircraft surfaces specifically for the purposes of avoiding radar detection.

25. The method of claim 13 wherein said step of analyzing further comprises the step of non-destructively detecting the presence of moisture in building materials including wood and gypsum wallboard.

26. A system for non-destructively characterizing the dielectric properties of materials associated with a target, comprising:
    a microwave energy source for producing primary microwave energy at about 24 Gigahertz;

a waveguide for directing said primary microwave energy towards a target;

a receiver for receiving and measuring secondary microwave energy reflected from said target and associated with said primary microwave energy;

a microprocessor programmed for analyzing the secondary microwave energy; and an indicator for providing results of microprocessor analysis.

27. The system of claim 26 including a portable, handheld system.

28. The system of claim 26 further comprising:

a truck assembly for adjustably maintaining said waveguide over said target.

29. The system of claim 28, said truck assembly further comprising wheels for enabling said truck assembly to be maneuvered over a surface associated with said target.

30. The system of claim 26, said indicator further comprising:

at least one light bar indicator for indicating a presence of corrosion and corrosion damage on said target.

31. The system of claim 26, further comprising a marking device for marking said target where corrosion or corrosion damage is indicated.

32. A system for non-destructively characterizing the dielectric properties of materials associated with a target, comprising:

a microwave energy source for producing microwave energy;

a waveguide for directing said primary microwave energy towards a target;

a receiver for receiving microwave energy reflected off said target;

an analyzer for assessing the difference between incident and reflected microwave signals received by said receiver to determine the presence of corrosion within a target or a targeted area associated with a target; and an indicator for providing results of microprocessor analysis.

33. The system of claim 32 further comprising:

a truck assembly for adjustably maintaining said waveguide over said target.

34. The system of claim 32, said truck assembly further comprising wheels for enabling said truck assembly to maneuvered over a surface associated with said target.

35. The system of claim 32, said indicator further comprising:

at least one light bar indicator for indicating a presence of corrosion and corrosion damage on said target.

36. The system of claim 32, further comprising a marking device for marking said target where corrosion in indicated.

37. The system of claim 32 wherein said analyzer is a microprocessor and said indicator is a display.

38. The system of claim 37 including memory for storing measurement data.

39. The system of claim 38, said truck assembly for adjustably supporting the system at uniform distances above said target.

* * * * *